United States Patent
Schouenborg et al.

(12) United States Patent (10) Patent No.: US 11,890,464 B2
(45) Date of Patent: Feb. 6, 2024

(54) HAEMORRHAGE AVOIDING MICROELECTRODE

(71) Applicant: NEURONANO AB, Karlshamn (SE)

(72) Inventors: Jens Schouenborg, Lund (SE); Mohsin Mohammed, Lund (SE)

(73) Assignee: NEURONANO AB

( * ) Notice: Subject to any disclaimer, the term of this patent is extended or adjusted under 35 U.S.C. 154(b) by 1510 days.

(21) Appl. No.: 15/778,041

(22) PCT Filed: Nov. 21, 2016

(86) PCT No.: PCT/SE2016/000072
§ 371 (c)(1),
(2) Date: May 22, 2018

(87) PCT Pub. No.: WO2017/095288
PCT Pub. Date: Jun. 8, 2017

(65) Prior Publication Data
US 2018/0369572 A1 Dec. 27, 2018

(30) Foreign Application Priority Data

Nov. 30, 2015 (SE) .................................. 1500491-4

(51) Int. Cl.
*A61N 1/05* (2006.01)
*A61B 5/24* (2021.01)
(Continued)

(52) U.S. Cl.
CPC .............. *A61N 1/0551* (2013.01); *A61B 5/24* (2021.01); *A61B 5/263* (2021.01); *A61N 1/0529* (2013.01);
(Continued)

(58) Field of Classification Search
CPC .............................. A61N 1/0551; A61B 5/263
See application file for complete search history.

(56) References Cited

U.S. PATENT DOCUMENTS

| | | | | |
|---|---|---|---|---|
| 4,827,940 A | * | 5/1989 | Mayer | A61B 5/283 600/377 |
| 6,360,129 B1 | * | 3/2002 | Ley | A61N 1/0573 600/375 |

(Continued)

FOREIGN PATENT DOCUMENTS

| | | |
|---|---|---|
| CN | 1671330 A | 9/2005 |
| CN | 102334988 A | 2/2012 |

(Continued)

OTHER PUBLICATIONS

Chinese Office Action, dated May 8, 2021, issued in corresponding Chinese Patent Application No. 201680069979.5. English translation. Total 39 pages.

(Continued)

*Primary Examiner* — Eric D. Bertram
(74) *Attorney, Agent, or Firm* — OSTROLENK FABER LLP (57) ABSTRACT

A microelectrode comprises an oblong electrically conducting electrode body covered by distal and proximal sections of a layer of insulating material except for an annular contact section disposed between them, a blunt distal bulge at the distal end of a radial extension substantially greater than that of the proximal section of non-conducting material. For implantation into soft tissue the microelectrode is provided with a support of a material dissolvable in body fluid. Also disclosed is a set of microelectrodes sharing such support, a method of manufacture of the microelectrode and the set, and uses of the microelectrode and the set.

31 Claims, 10 Drawing Sheets

(51) Int. Cl.
*A61B 5/263* (2021.01)
*A61B 17/34* (2006.01)

(52) U.S. Cl.
CPC ..... *A61B 17/3468* (2013.01); *A61B 2562/125* (2013.01)

(56) References Cited

U.S. PATENT DOCUMENTS

| | | | |
|---|---|---|---|
| 8,682,450 B2 | 3/2014 | Min | |
| 9,878,147 B2 | 1/2018 | Ek | |
| 2006/0155345 A1 | 7/2006 | Williams et al. | 607/48 |
| 2007/0088208 A1* | 4/2007 | Yasuzawa | A61N 1/05 607/2 |
| 2008/0009927 A1 | 1/2008 | Vilims | 607/115 |
| 2008/0140152 A1 | 6/2008 | Imran et al. | 607/46 |
| 2012/0203245 A1 | 8/2012 | Imabayashi | |
| 2012/0253442 A1 | 10/2012 | Gliner et al. | 607/116 |
| 2013/0190851 A1* | 7/2013 | Schouenborg | A61N 1/0536 607/116 |
| 2014/0039238 A1 | 2/2014 | Min | |
| 2014/0163659 A1 | 6/2014 | Boling | 607/116 |
| 2014/0323948 A1 | 10/2014 | Ek et al. | 604/20 |
| 2014/0371564 A1 | 12/2014 | Anikeeva et al. | 600/377 |
| 2015/0151107 A1* | 6/2015 | Schouenborg | A61B 5/24 604/20 |

FOREIGN PATENT DOCUMENTS

| | | |
|---|---|---|
| CN | 102458564 A | 5/2012 |
| CN | 103153392 A | 6/2013 |
| CN | 104411360 A | 3/2015 |
| WO | WO 2009/075625 A1 | 6/2009 |
| WO | WO 2010/055421 A1 | 5/2010 |
| WO | WO 2013/191612 A1 | 12/2013 |
| WO | WO 2015/042339 A1 | 3/2015 |

OTHER PUBLICATIONS

Israeli Office Action, dated May 4, 2021, issued in corresponding Israeli Patent Application No. 259632. Partial translation. Total 5 pages.
International Search Report dated Mar. 15, 2017 in corresponding PCT International Application No. PCT/SE2016/000072.
Written Opinion dated Mar. 15, 2017 in corresponding PCT International Application No. PCT/SE2016/000072.
Office Action dated Dec. 16, 2022 issued in corresponding Canadian Patent Application No. 3,006,644.

* cited by examiner

HAEMORRHAGE AVOIDING MICROELECTRODE

CROSS-REFERENCE TO RELATED APPLICATIONS

The present application is a 35 U.S.C. §§ 371 national phase conversion of PCT/SE2016/000072, filed Nov. 21, 2016, which claims priority to Swedish Patent Application No. 1500491-4, filed Nov. 30, 2015, the contents of which are incorporated herein by reference. The PCT International Application was published in the English language.

FIELD OF THE INVENTION

The present invention relates to a proto-microelectrode which avoids haemorrhage during implantation into soft tissue, in particular nervous tissue, to a microelectrode formed from the proto-microelectrode upon implantation, and to their manufacture and use. The present invention furthermore relates to sets of such proto-microelectrodes and microelectrodes, and to their manufacture, implantation, and use.

BACKGROUND OF THE INVENTION

During implantation of microelectrodes into nervous tissue by inserting them with their distal end foremost there is a substantial risk of damaging penetration of blood vessel. There is also a risk of implanted microelectrodes damaging blood vessels or cells.

While not being life threatening micro-haemorrhage resulting from such damage does substantially impair the analytical or therapeutic performance of the microelectrode or, if haemorrhage is caused by a microelectrode pertaining to a set, also the analytical or therapeutic performance of neighbouring electrodes.

In the event that several microelectrodes are used to treat a neurological condition or in research, identification of their disposition in tissue is called for, in particular in respect of anatomical landmarks such as nuclei or sub-nuclei. Due to, i.a., their small size it is difficult to determine the position of single microelectrodes by means of current non-invasive techniques such as Magnetic Resonance Imaging (MRI), Computer Tomography (CT), and Doppler techniques. In regard of an implanted set of microelectrodes it is therefore difficult or impossible to determine their positions in respect of each other and of anatomical landmarks.

Due to their flexibility thin oblong microelectrodes cannot be implanted by inserting them into soft tissue in the absence of a support making them sufficiently rigid for this purpose, they are even more difficult to implant in a desired disposition in respect of a selected target in the brain like a nerve cell. The targeted disposition of a set of such microelectrodes therefore requires measures not readily available in the art, such as avoiding them damaging a blood vessel and to spread them out in the tissue in a desired manner.

OBJECTS OF THE INVENTION

A primary object of the present invention is to provide a microelectrode that does not damage blood vessels during implantation by insertion into soft tissue and/or during its disposition in non-static soft tissue or, at least, to provide a microelectrode of which the risk of damage is substantially reduced. The soft tissue concerned is primarily nervous tissue, in particular brain or spinal cord tissue, but also endocrine tissue such tissue of the pituitary, pineal, thyroid, parathyroid, and adrenal glands, testes and ovaries tissue, and pancreatic islets of Langerhans tissue.

Another primary object of the present invention is to provide a microelectrode that minimizes cell damage.

Another object of the present invention is to provide a set of such microelectrodes.

Still another object of the present invention is to provide a means for determining the position of a microelectrode pertaining to a set of implanted microelectrodes in respect of any other microelectrode and/or an anatomical landmark like a particular nerve cell or a nucleus.

A further object of the present invention is to provide a set of such microelectrodes of which each electrode can be identified in situ upon insertion.

A still further object of the invention is to provide a method of manufacture of the microelectrode of the invention and of a set comprising two or more microelectrodes of the invention.

Additional objects of the present invention will become apparent from the study of the following summary of the invention, the description of preferred embodiments thereof, and the appended claims.

SUMMARY OF THE INVENTION

The microelectrode of the invention is of such kind that it only can be disposed in soft tissue by means of a rigid support. In this application the combination of microelectrode and rigid support is termed proto-microelectrode. Upon implantation the rigid support is removed by dissolution in body fluid and the microelectrode of the invention is formed in situ.

Soft tissue according to the invention is, in particular, nervous tissue such as brain tissue, spinal cord tissue, dorsal root ganglia and peripheral nerves but includes also body fluid and membranes enclosing such tissue.

According to the present invention is provided a microelectrode for implantation into soft tissue, in particular nervous tissue, comprising an oblong electrode body of an electrically conducting material having a proximal end and a distal end, wherein the electrode body is covered by a layer of first insulating material except for at an annular contact section thereof disposed between a distal section extending from the distal end in a proximal direction and a proximal section extending from the annular section to the proximal end, the layer of insulating material on the distal terminal section extending distally of the distal end of the electrode body so as to fully enclose the distal end to form a blunt distal bulge or wherein the layer of first insulating material on the distal terminal section is covered or substituted by a layer of second insulating material forming the bulge. The bulge has a radial extension that is substantially greater than the radial extension of the layer of non-conducting material disposed on the proximal section.

According to the invention is furthermore provided a microelectrode for implantation into soft tissue, in particular nervous or endocrine tissue, comprising an oblong electrode body of electrically conducting material having a proximal end and a distal end, the body comprising insulated distal and proximal sections extending from the distal and proximal ends, the distal section optionally comprising a bulb at its distal end; wherein the distal and proximal sections are separated by an annular section, wherein the proximal section is covered by a layer of first insulating material and wherein the electrode comprises a blunt distal terminal bulge formed by one of: layer of first insulating material on the distal section; layer of first insulating material on the distal section covered or fully or partly substituted by a layer of a second insulating material; layer of first insulating material and/or second insulating material on the bulb; wherein the bulge has a radial extension substantially greater than that of the proximal section covered by layer of first insulating material.

According to a preferred aspect of the invention, a microelectrode comprises two or more annular sections separated by insulated section(s). It is preferred for the two or more annular sections to be arranged in close vicinity of each other, such as within a section of the electrode body extending axially by 20% or 10% or 5% or 2% of the axial extension (length) of the electrode body.

It is preferred for the microelectrode body to be rotationally symmetric. It is also preferred for the microelectrode body to be flexible, in particular resiliently flexible. According an advantageous aspect of the invention the electrode body is flexible and curved and of a shape so as to be of rotationally symmetric form in a straight conformation.

A distal face of the distal bulge can be about hemispherical or hemi-elliptic or of paraboloid or hyperboloid form, the distal bulge comprising a circular or elliptic base facing in a proximal direction and being centered on the axis of rotational symmetry.

According to a preferred aspect of the invention the radial extension of the bulge is preferably greater by 50% or more, in particular by 100% or more, or 1000% or more than the radial extension of the layer of first insulating material on the proximal section.

According to another preferred aspect of the invention the axial length ratio of the distal section to the proximal section is preferably 1:2 or 1:5 or more, in particular 1:10 or more, and may even be 1:20 or more and 1:50 or more. It is preferred for the axial length of the annular section to be 10% or less, in particular 5% or 2% or 1% or less of the length of the electrode body.

According to a further preferred aspect of the invention an insulating material on the distal section is of a material different from that on the proximal section. It is preferred for an insulating material on the distal section to be covered by a layer of material capable of swelling in contact with aqueous body fluid, in particular swelling at body temperature to reach an equilibrium swollen state of a radial extension greater by a factor of 2 or 5 and even of 10 or more than that of the non-swollen material. The material capable of swelling has a preferred Bloom strength of from 200 to 300 or more, in particular from 200 to 350, most preferred of about 300.

According to another preferred aspect of the invention an insulating material on the distal section is resilient, in particular resilient by comprising closed gas-filled cells.

According to a preferred aspect of the invention a bulge material or insulating material comprises an agent to improve the visibility of a microelectrode of the invention in MRI, for instance an agent comprising or consisting of ferromagnetic particles.

The microelectrode of the invention can be attached or be attachable to flexible insulated electrical conductor in a conducting manner, the attachment is to the electrode body being preferably at or near the proximal end thereof.

The electrode body of the microelectrode of the invention consists of a metal or comprises a metal or consists of or comprises an electrically conducting polymer.

According to the present invention is also disclosed a proto-microelectrode comprising or consisting of the microelectrode of the invention and a biocompatible solid support material. The support material is attached to the microelectrode in a manner to stabilize it sufficiently so as to allow implantation of the microelectrode into soft tissue by insertion with its distal end foremost. According to an important aspect of the invention the support material is rigid; it is furthermore dissolvable in body fluid. The support material may enclose the microelectrode partially or fully.

The support material can consist of or comprise carbohydrate and/or protein and optionally comprises a pharmacologically active agent selected from the group consisting of coagulant, anticoagulant, antibiotic, osmotic pressure adjusting agent, anti-inflammatory agent, nutrient, factor stimulating growth, factor stimulating cell differentiation, hormone.

According to the present invention is furthermore disclosed a set of axially aligned proto-microelectrodes of the invention sharing the support material, that is, a proto-set of microelectrodes. The terms proto-set of microelectrodes and set of proto-microelectrodes thus are used indiscriminatingly in this application. The microelectrodes can be disposed in the proto-set in parallel or in a mode fanning out in a distal direction, such as by an angle of 10 degrees or 15 degrees in respect of a centrally disposed electrode used as reference. A microelectrode of the proto-set can comprise one or more additional subsections of second insulating material of a radial extension substantially greater than that of the insulating layer on the proximal section. The subsections can be disposed on the electrode body so as to be comprised by the distal and/or the proximal section. The subsections can be fully separated or be separated by intermediate sections of smaller radial extension, which radial extension is, however, greater than the radial extension of the first insulating layer.

According to a preferred aspect of the invention a proto-set of microelectrodes can comprise an expandable material capable of swelling in body fluid. The expandable material is disposed between two or more microelectrodes in the proximity of their distal ends. According to an important aspect of the invention the dissolution rate of the expandable material in body fluid is lower than the dissolution rate of the support material. The expandable material has a preferred Bloom strength of from 80 to 200, in particular of about 100 to 150, that is, a Bloom strength inferior to that of the material capable of swelling in contact with aqueous body fluid disposed on a layer of first and/or second insulating material of a distal bulge.

According to a further preferred aspect of the invention is disclosed a proto-set wherein a distal bulge of insulating material of one microelectrode is of non-spherical form. The distal bulge is disposed on a distal terminal section of the electrode and in a manner so as to slant radially outwardly in respect of the electrode body axis. This makes the distal bulge display a front face, which is the face exhibited by the bulge in a proximal view, that slants radially outwardly.

To allow identification by radiative means of single electrodes pertaining of a set upon implantation of the corresponding proto-set and dissolution of the support material, the electrodes are provided with different numbers of subsections of substantially greater diameter than that of the insulating layer on the proximal section differing in their radial extension. Alternatively the microelectrodes of a set can be distinguished by making the composition of the insulating material forming their distal bulges and/or forming one or more of said subsections differ.

Furthermore disclosed herein is the use of a microelectrode, a proto-microelectrode and a set of proto-microelectrodes of the invention in a method comprising electrical stimulation of cells, in particular nerve cells, and in a method comprising monitoring the electrical activity of such cells.

Additionally disclosed herein is the use of a microelectrode, of a proto-microelectrode, and of a of set of proto-microelectrodes of the invention in a method of treating a condition comprising an aberrant function of cells in brain tissue, spinal cord tissue, dorsal root ganglia and peripheral nerves by electrical stimulation and in monitoring the electrical activity of cells in such tissue.

A microelectrode pertaining to a set or proto-set of microelectrodes of the invention need not be of equal length. A proto-set and a corresponding set of the invention thus can comprise two or more microelectrodes of different length.

To facilitate implantation into soft tissue by insertion a proto-microelectrode or a proto-set of microelectrodes of the invention can comprise a friction reducing coat on the support material.

The invention will now be explained in more detail by reference to a number of preferred embodiments thereof illustrated in a rough drawing, of which the figures are not to scale for reasons of clarity. In general, the radial extension of an illustrated microelectrode is exaggerated in relation to its axial extension. The illustrated microelectrodes are rotationally symmetric or at least substantially rotationally symmetric.

DESCRIPTION OF THE FIGURES

FIG. 4b is a radial section (S-S, FIG. 4a) through the set of proto-microelectrodes of FIG. 4a;

FIG. 4c is a radial section through another set of proto-microelectrodes (not shown in axial section), the section corresponding to that of FIG. 4b;

FIGS. 9-9c illustrated the process of insertion of the proto-set of microelectrodes of the invention into soft tissue; wherein:

DESCRIPTION OF PREFERRED EMBODIMENTS

Example 1. Microelectrodes

FIGS. 1a-1f and 7-7b illustrate nine embodiments of the microelectrode of the invention.

Figure 1A:
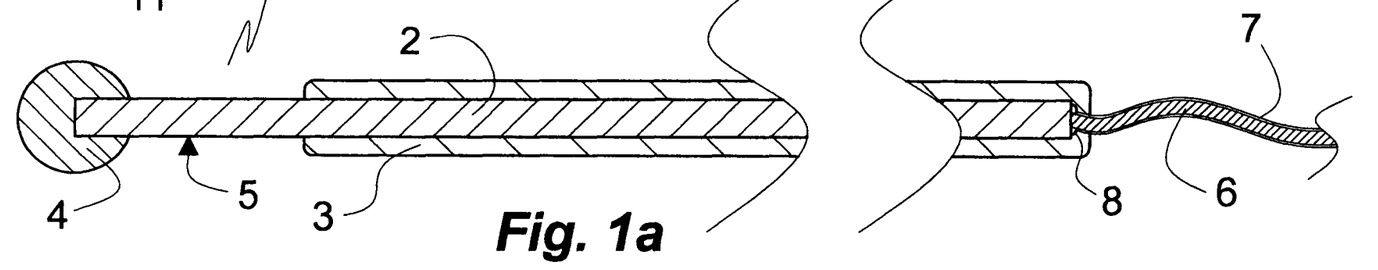
FIG. 1a is an axial section through a first rotationally symmetric embodiment of the microelectrode of the invention.

The microelectrode 1 of FIG. 1a comprises an oblong cylindrical electrode body 2 of metal or electrically conducting polymer. The electrode body 2 is electrically insulated except for an annular zone 5 disposed near its distal end from which it is separated by a sphere 4 of polymer material surrounding and enclosing the distal end of the electrode body 2. Starting at the proximal border of the annular zone 5 the electrode body 2 is electrically insulated by a thin layer 3 of polymer material, which extends to and encloses the proximal end of the electrode body 2. The proximal end of the electrode body 2 is in electrical contact with an insulated 6 flexible wire 7 attached to the electrode body 2 by solder 8 or welding.

Figure 1B:
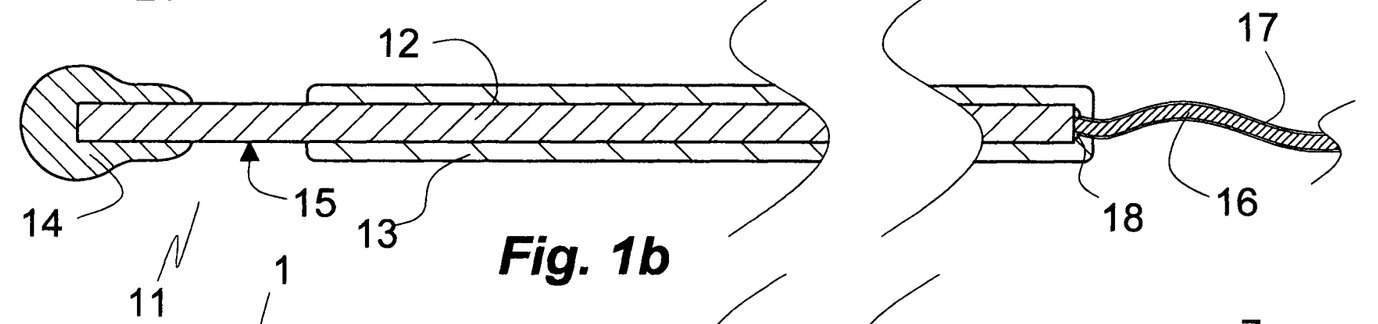
FIG. 1b is an axial section through a second rotationally symmetric embodiment of the microelectrode of the invention.

The microelectrode 11 of FIG. 1b differs from that 1 of FIG. 1a by the sphere 4 being substituted by a pear-like distal terminal bulge 14 of polymer material. Reference numbers 12, 13, 15, 16, 17, and 18 designate elements/features corresponding to reference numbers 2, 3, and 5 through 8 of FIG. 1a. In general, the polymer material used for forming a bulge is a material with insulating properties although these properties are only effective if the bulge is disposed on the naked electrode body 2 and not the thin insulating layer 3 covering sections of the electrode body 2.

Figure 1C:
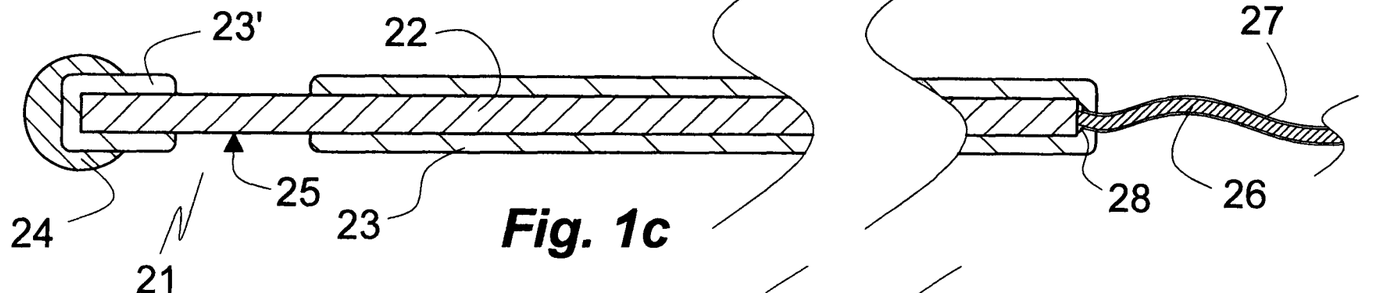
FIG. 1c is an axial section through a third rotationally symmetric embodiment of the microelectrode of the invention.

The microelectrode 21 of FIG. 1c differs from that 1 of FIG. 1a by the thin layer of insulating material 23, 23' on the electrode body 22 being interrupted by near the distal end to form a proximal portion 23 and a distal portion 23' delimitating an annular electrode zone 25 disposed between them, the distal portion 23', a sphere 24 of insulating polymer material surrounding and enclosing the distal end of the electrode body 22 and a terminal section of the distal portion 23' of insulating material.

Figure 1D:
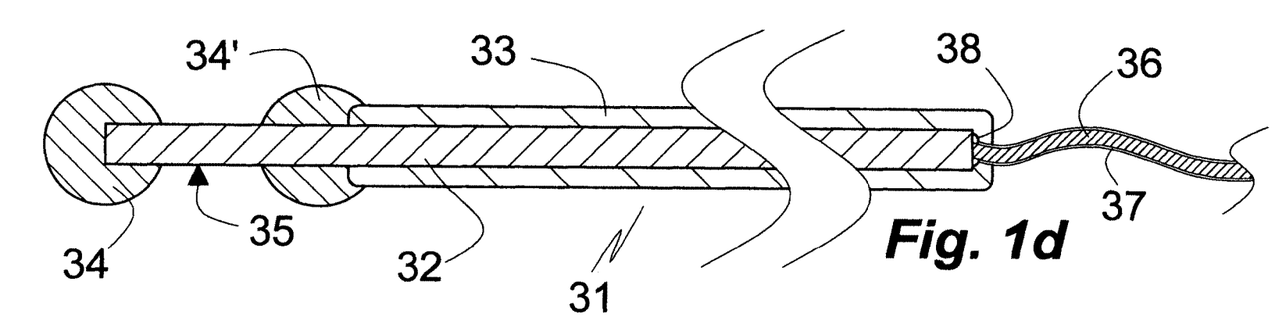
FIG. 1d is an axial section through a fourth rotationally symmetric embodiment of the microelectrode of the invention.

The microelectrode 31 of FIG. 1d differs from the microelectrode 1 of FIG. 1a by a second sphere of polymer material disposed around the proximal end of the thin layer of insulating polymer material 33 extending from the proximal end of the electrode body 32 to the proximal border of the annular electrode zone 35.

Figure 1E:
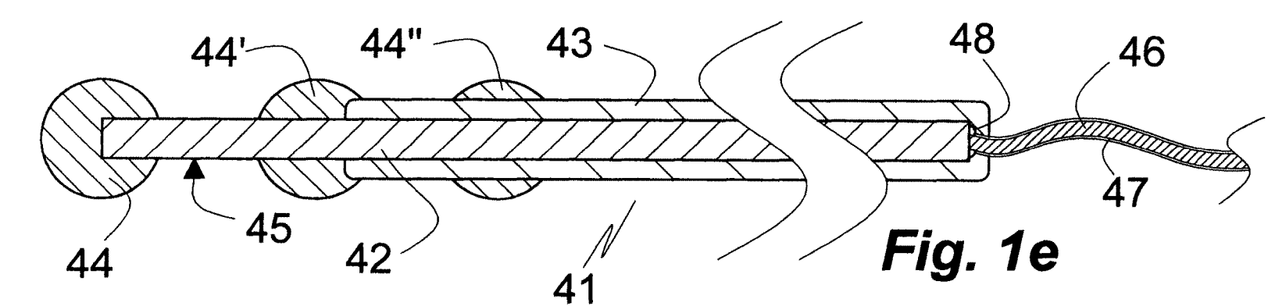
FIG. 1e is an axial section through a fifth rotationally symmetric embodiment of the microelectrode of the invention.
Figure 1F:
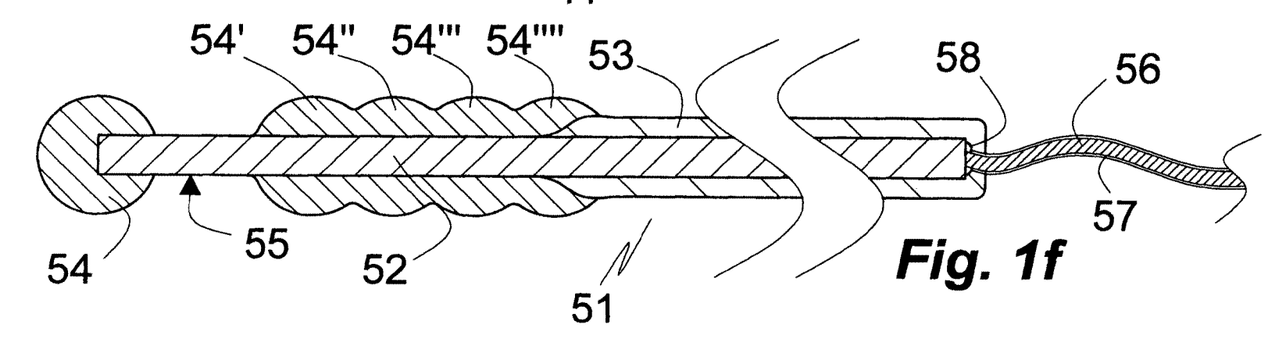
FIG. 1f is an axial section through a sixth rotationally symmetric embodiment of the microelectrode of the invention.

The microelectrode 41 of FIG. 1e differs from that 31 of FIG. 1d by a third sphere 44" arranged in addition to the first 44 and second 44' sphere, the third sphere 44" being disposed proximally of the second sphere 44' on a portion of the electrode body 42 covered by a thin layer 43 of insulating material. Reference numbers 45-48 designate elements/features corresponding to elements/features 35-38 of the embodiment The microelectrode 51 of FIG. 1f differs from that (1d) of FIG. 1a by four partially merged spheres 54', 54", 54''', 54'''' of same diameter disposed on the electrode body 52, the first (distal) sphere 54' proximally delimiting the annular electrode zone 55 whereas the fourth sphere 54'''' surrounds and seals the distal end of the thin insulating layer 53 on the proximal portion of the electrode body 52. Features 56-58 correspond to features 36-38 of the embodiment of FIG. 1d.

Figure 7:
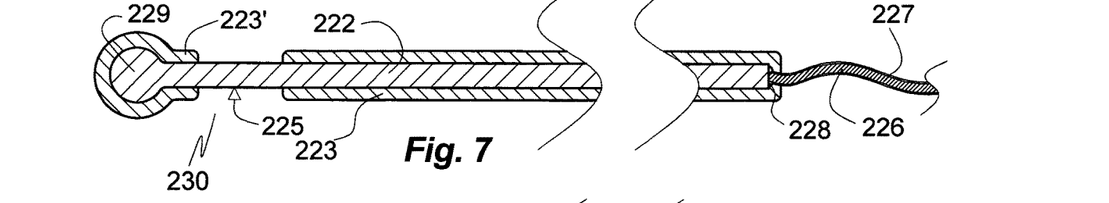
FIG. 7 is an axial section through a seventh rotationally symmetric embodiment of the microelectrode of the invention.

The microelectrode 230 of FIG. 7 comprises an oblong cylindrical electrode body 222 of metal or electrically conducting polymer. The electrode body 222 is insulated by a polymer layer 223, 223' except for an annular zone 225 disposed near its distal end. The distal end of the electrode body 222 is radially widened so as to form a bulb 229. The bulb 229 and a short cylindrical section of the electrode body 222 extending between the bulb 229 and the annular zone 225 are covered by a distal section 223' of the polymer layer so as to form a bulge 223', 229. A proximal section 223 of the polymer layer extends from the annular zone 225 to the proximal end of the electrode body 222, and surrounds and encloses it. The proximal end of the electrode body 222 is in electrical contact with an insulated 226 flexible wire 227 attached to the electrode body 222 by solder 228 or by welding. The bulb 229 improves the adherence of the polymer layer 223' to the distal portion of the electrode body 222, which is particularly important in the event the electrode 230 is withdrawn from the tissue; this minimizes the risk of the polymer layer 231' coming loose and being left in the tissue.

Figure 7A:
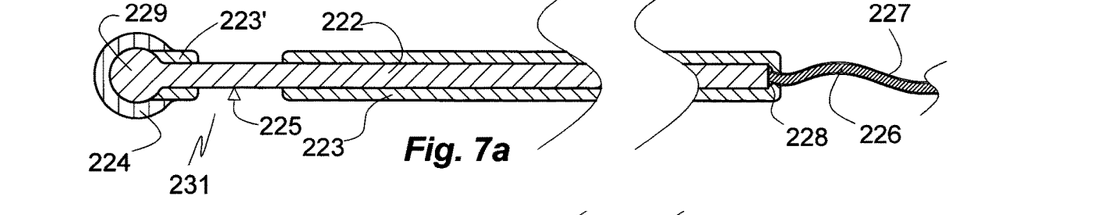
FIG. 7a is an axial section through a eight rotationally symmetric embodiment of the microelectrode of the invention.

The microelectrode 231 of FIG. 7a differs from the microelectrode 230 of FIG. 7 by the bulge 231', 224, 229 being formed by the bulb 229 covered by an insulating material 224 different from the insulating material 231 on the proximal section and insulating material 231' of same kind as that of the proximal section disposed on a short distal section extending between the distal end of the annular zone 225 and the bulb 229. The microelectrode 232 of FIG. 7b differs from the microelectrode 230 of FIG. 7 by the bulge 224, 229 being formed by the bulb 229 covered by an insulating material 224 different from the insulating material 231 on the proximal section and extending to the distal end of the annular zone 225.

Figure 7B:
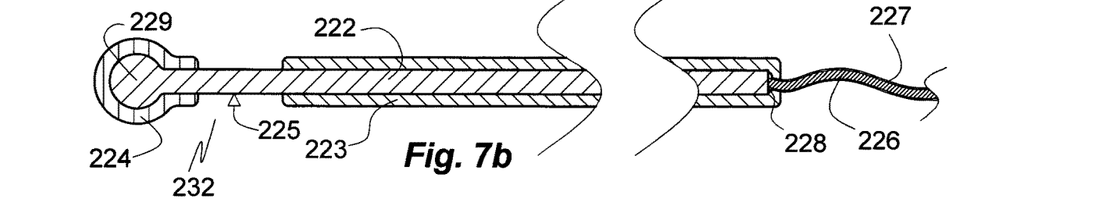
FIG. 7b is an axial section through a ninth rotationally symmetric embodiment of the microelectrode of the invention.
Figure 7C:
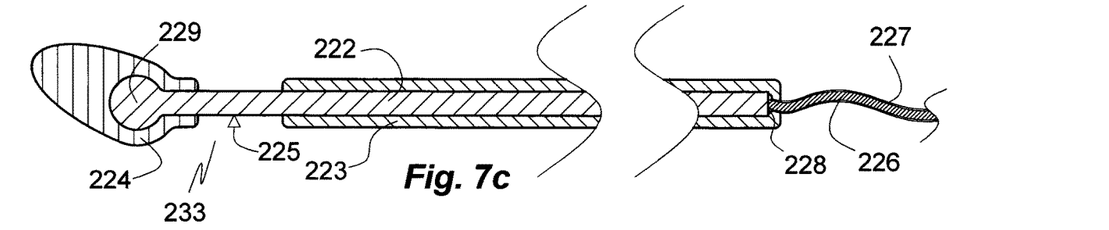
FIG. 7c is an axial section through a tenth embodiment of the microelectrode of the invention, which is rotationally symmetric except for its distal head or bulge.
Figure 8:
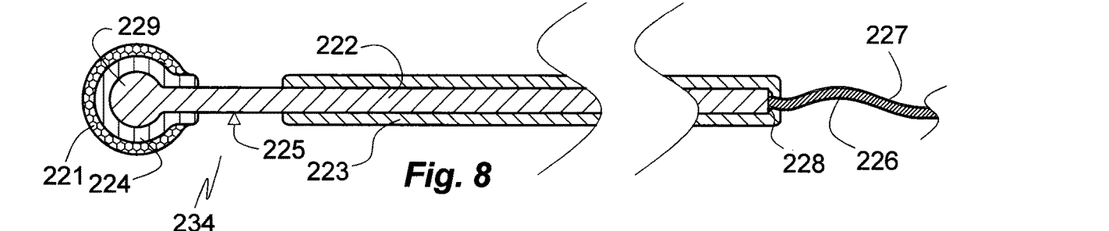
FIGS. 8, 8a are axial sections through the microelectrode of FIG. 7b comprising a layer of gel-forming material on its distal terminal bulge prior and upon contact with aqueous body fluid, respectively.
Figure 8A:
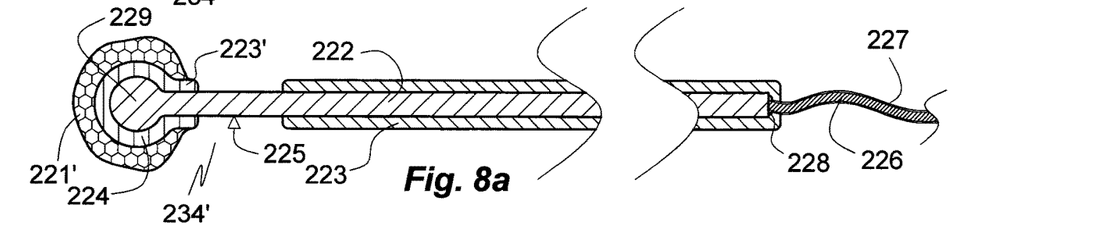

The microelectrode 233 of FIG. 8 differs from that of FIG. 7b by the insulating material 224 of the bulge 224, 229 being covered by a layer 221 of dry gelatin. Upon contact with aqueous body fluid the gelatin layer 221 absorbs water and is transformed to a gel forming an expanded gellous layer 221' on the insulating material 224. The gellous layer 221' is not permanent but is dissolved or degraded over time, the rate of dissolution/degradation being dependent on its physical and chemical properties, such as its degree of crosslinking.

Example 2. Sets of Proto-Microelectrodes

Figure 2A:
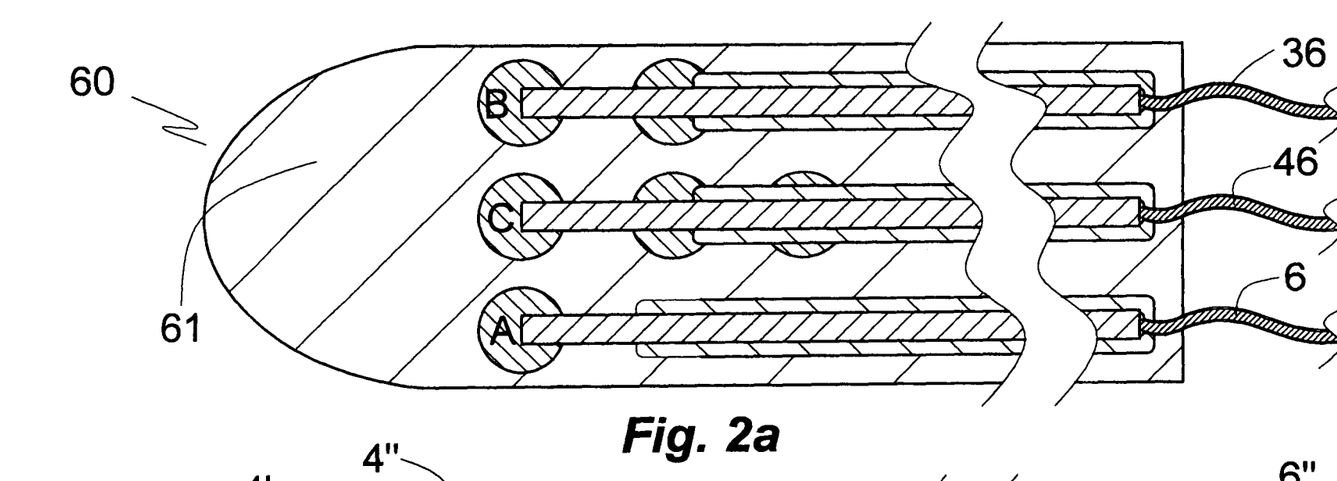
FIG. 2a is an axial section through a first embodiment of a set of proto-microelectrodes of the invention comprising three different rotationally symmetric microelectrodes.

The set of proto-microelectrodes 60 of the invention shown in FIG. 2a comprises three microelectrodes A, B, C, which are identical with the microelectrodes 1, 31, 41, respectively, of FIGS. 1a, 1d, and 1e. Except for their insulated flexible wires 6, 36, 46 the microelectrodes A, B, C are fully embedded in a rigid support material 61 that is soluble in aqueous body fluid. The layer of rigid support material embedding the set of microelectrodes A, B, C is rotationally symmetric about an axis (not shown) corresponding to that of the central microelectrode C. The material 61 consists or comprises biocompatible carbohydrate or protein that is soluble in body fluid. The microelectrodes A, B, C are aligned in parallel and of about same length. It is however within the ambit of the invention to use microelectrodes of different length.

Figure 2B:
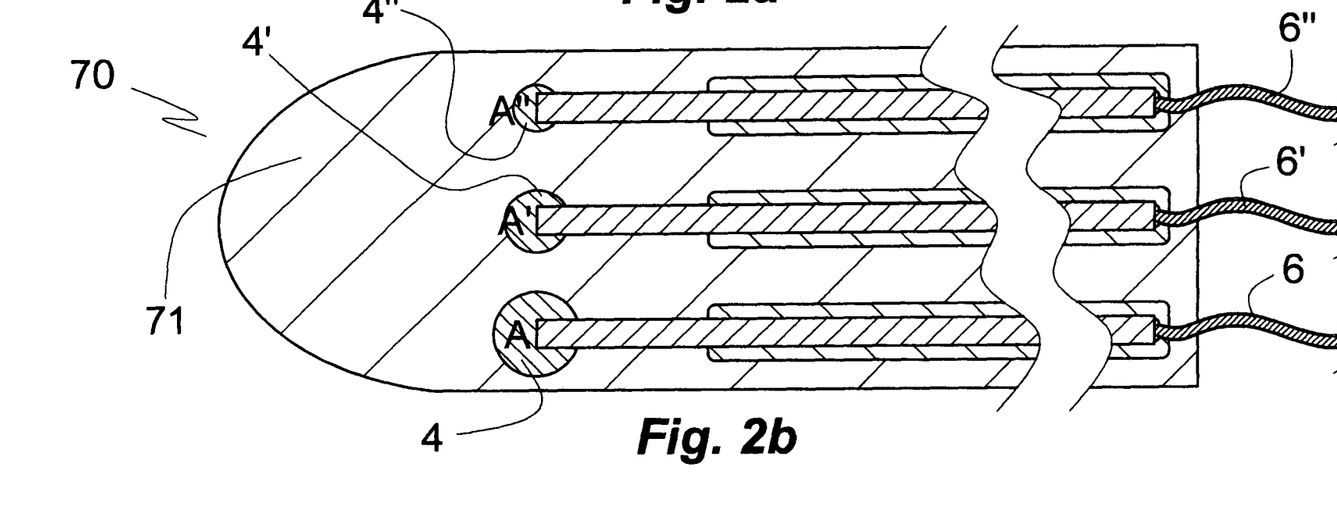
FIG. 2b is an axial section through a second embodiment of a set of proto-microelectrodes of the invention comprising three different rotationally symmetric microelectrodes.

Another embodiment of the set of proto-microelectrodes of the invention is shown in FIG. 2b. The proto-set 70 comprises three microelectrodes A, A', A" of about equal length disposed in parallel. The microelectrodes A, A', A" are identical with the microelectrode 1 of FIG. 1a, except for the spheres 4', 4" of microelectrodes A', A" being consecutively smaller than the sphere 4 of microelectrode A. Except for their insulated flexible wires 6, 6', 6" attached at their proximal ends the microelectrodes A, A', A" are embedded in a rotationally symmetric rigid support material in a manner that the layer of support material 71 is centred about the central microelectrode A', that is, has an axis of rotation superimposed on that of the axis of rotationally symmetric microelectrode A'. Useful layer 71 materials comprise low or medium molecular weight carbohydrate or protein.

Figure 3:
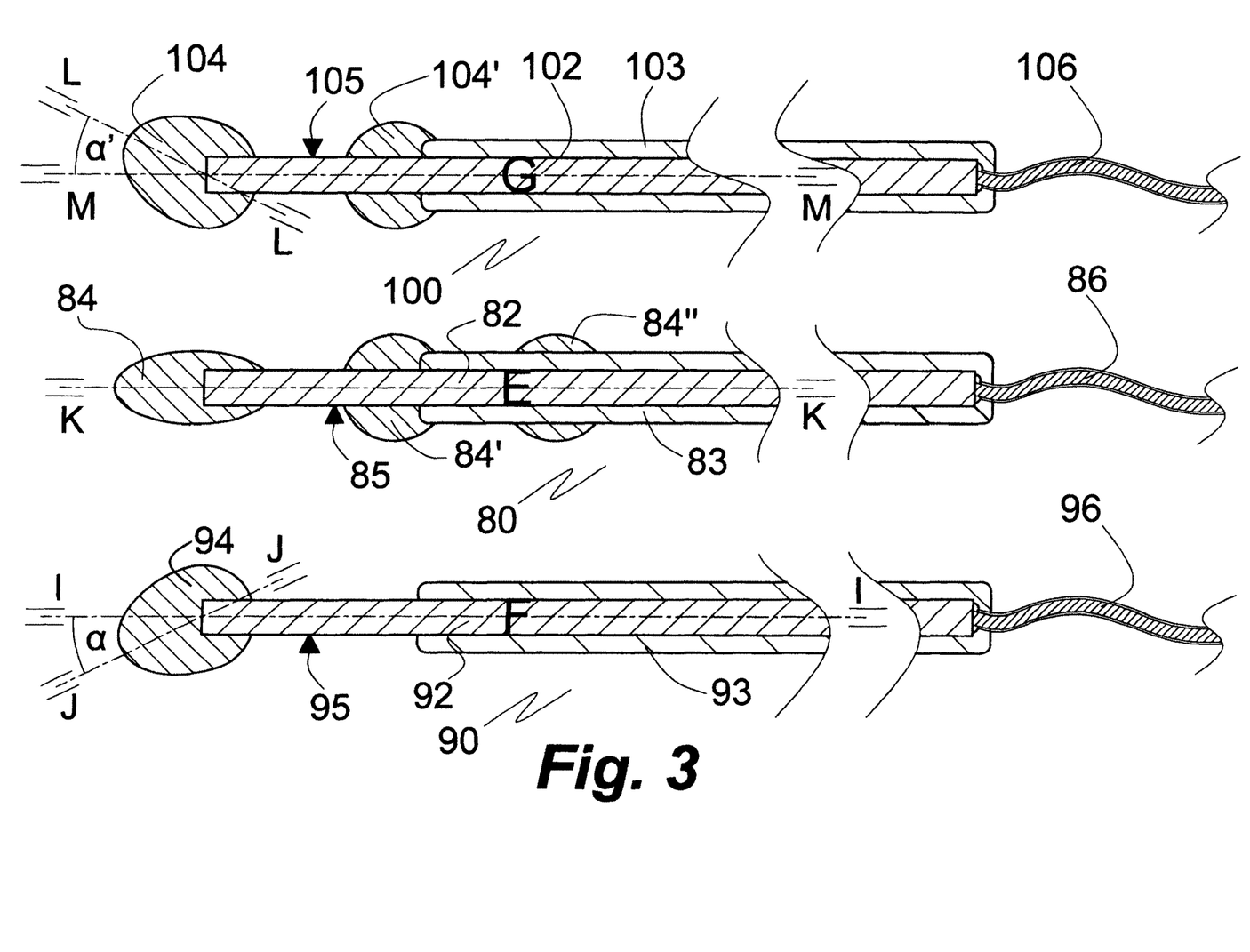
FIG. 3 is an axial section through a set of three microelectrodes of the invention of which one is rotationally symmetric and the other two are rotationally symmetric except for at their distal end portion.
Figure 3A:
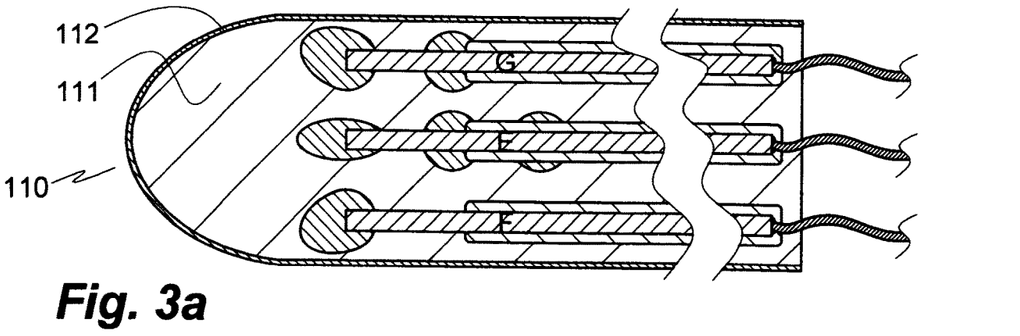
FIG. 3a is a set of proto-microelectrodes corresponding to the set of microelectrodes of FIG. 3, enclosed in a rigid support material dissolvable in body fluid, in the same axial (with regard to the set and to each individual electrode) section.

A further set 110 of microelectrodes is shown in FIG. 3a. Strictly speaking the set 110 is a proto-set of microelectrodes. The proto-set 110 comprises three microelectrodes 80, 90, 100 in the disposition of FIG. 3. The centrally disposed microelectrode 80 is of same design as microelectrode 41 of FIG. 1e except for its distal bulge 84 being ellipsoid in longitudinal section instead of the circular section of distal bulge 44 of FIG. 1e. The long axis of the distal bulge 84 K-K is aligned with the axis of electrode body 82, whereas the long axes J-J, L-L of the bulges 94 and 104 are not aligned with the axes I-I, M-M of electrode bodies 92, 102 but form an angle α, α' of about −30°, 30° with them.

The microelectrodes E, F, G of FIG. 3 are embedded in a layer 111 of same design and composition as that of the proto-set of microelectrodes of FIGS. 2a, 2b so as to form the proto-set of microelectrodes 110 illustrated in FIG. 3a. Except for its rear terminal face 113 the layer 111 is covered by a thin outer layer 112 of a friction reducing material, which dissolves or disintegrates upon insertion of the layer 111 of material soluble in body fluid comprising the proto-set of microelectrodes 110 into nervous tissue. The outer layer 112 can also protect the layer 111 material from premature dissolution prior to completion of insertion.

Figure 3B:
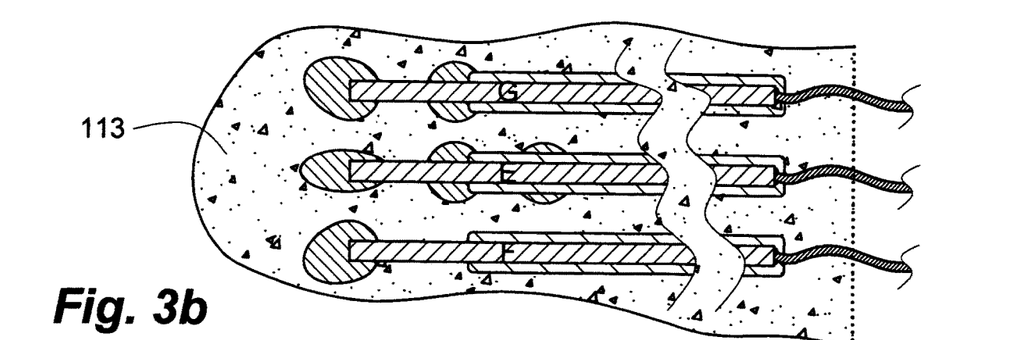
FIG. 3b illustrates the disposition of the set of microelectrodes of FIG. 3 formed upon the insertion of the set of proto-microelectrodes of FIG. 3a into nervous tissue and dissolution of the support material by body fluid, in the same axial section.

Upon insertion into nervous tissue 113 and dissolution of the layer 111 the state shown in FIG. 3b is reached. The microelectrodes E, G, F of the set formed in situ are disposed in the tissue 113 in about the same disposition as that of FIG. 3a.

Figure 3C:
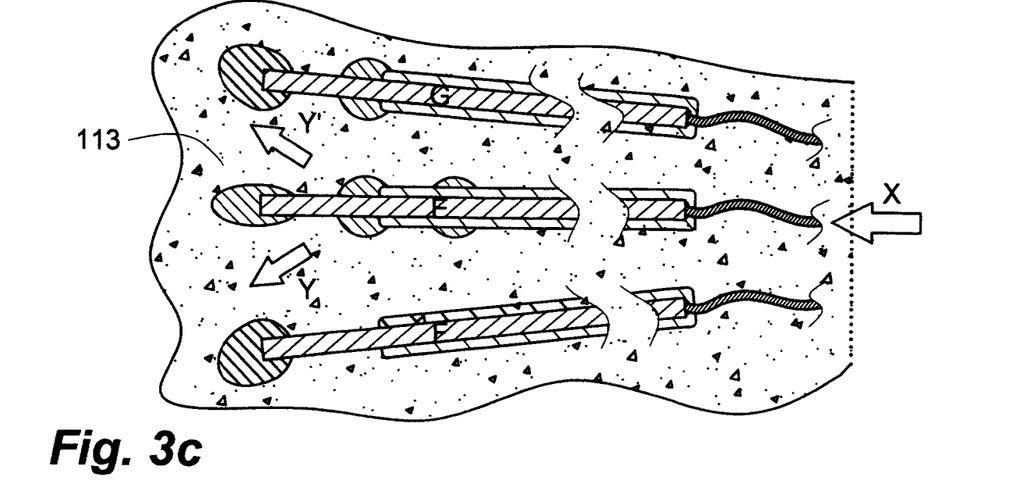
FIG. 3c illustrates the disposition of the electrodes of the set of FIG. 3 upon inserting them further into nervous tissue by an axial force acting on their proximal ends, in the same axial (with regard to the bundle and to each individual electrode) section.

During their further insertion by a force X acting about axially on each microelectrode E, F, G in a distal direction as indicated by arrow X, the centrally disposed microelectrode E is displaced in an axial, distal direction, whereas the flanking microelectrodes F and G are deflected away from the central electrode F as indicated by arrows Y, Y' to be disposed in the tissue in a skew axial direction. The deflection is caused by bulges 94, 104, which are disposed asymmetrically in regard of axis K-K of the central microelectrode axes E. This design allows to fan out peripherally disposed, axially aligned or about aligned members of a proto-set of microelectrodes once the support material immobilizing the set E, F, G has been dissolved upon insertion into nervous tissue. This arrangement provides the additional advantage of a small wound caused by the insertion allowing disposition of the distal microelectrode end portions over an area substantially wider than the wound area, that is, the area of the wound transverse to the direction of insertion of the bundle into nervous tissue.

Figure 4A:
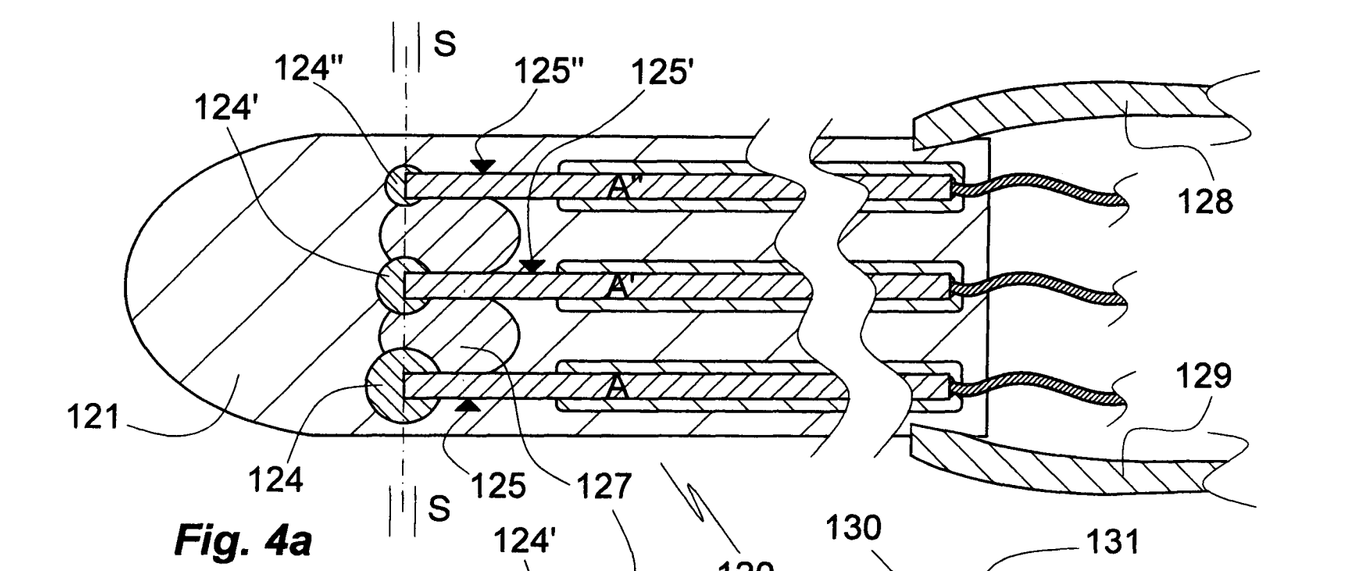
FIG. 4a illustrates another embodiment of the set of proto-microelectrodes of the invention enclosed in a rigid support material, which is dissolvable in body fluid, further comprising sections of a material forming a gel on contact with body fluid, disposed between the distal terminal portions of the electrodes, in an axial (R-R, FIG. 4b; with regard to the set and to each individual electrode) section.
Figures 4B, 4C:
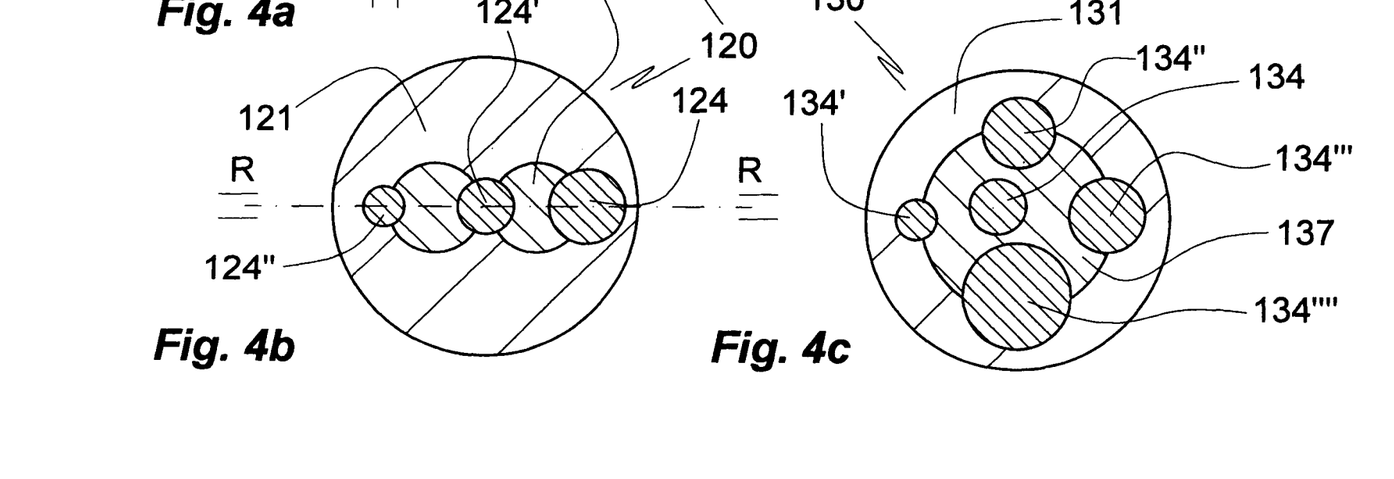

The third embodiment of the proto-set of microelectrodes of the invention shown in FIGS. 4a and 4b comprises three microelectrodes A, A', A" aligned in parallel and in a spaced configuration, of which microelectrode A is identical with that of FIG. 1a whereas the other microelectrodes A' and A" have distal terminal bulges 124', 124" of differing and, in respect of bulge 124 of microelectrode A, reduced diameter. In the space between distal terminal portions the pairs A, A' and A', A" are disposed inserts 127, 127' of a material, which swells on contact with body fluid. The axial extension of the inserts 127, 127' comprises part of that of the bulges 124, 124', 124" and of the annular, insulation free electrode body sections 125, 125', 125". Upon insertion of the proto-set 120 into nervous tissue and dissolution of the matrix 121 the inserts 127, 127' are contacted by body fluid, which they take up while swelling; their swelling pushes the distal terminal portions including the bulges 124, 124', 124" of the microelectrodes A, A', A" apart, so that their further insertion into the tissue results in pushing the outer microelectrodes A, A" away from the central microelectrode A' so as to make their distal portions fan out. The dispositional effect thus is similar to that of the embodiment of FIG. 3a. The position of each of the microelectrodes A, A', A" in neural tissue can be identified by tissue penetrating imaging techniques due to them differing in respect of the size of their distal terminal bulges 124, 124' 124". Insertion of the microelectrode proto-set 120 into neural tissue is accomplished by, for instance, use of a tongue-like instrument holding the bundle 120 at opposite lateral rear indentations by means of tongues 128, 129.

FIG. 4c illustrates a proto-set 130 of microelectrodes, which is a variation of the embodiment of FIGS. 4a, 4b. The proto-set 130 of microelectrodes comprises five microelectrodes covered by a rotationally symmetric support material 131 that is dissolvable in body fluid and of same shape as that of FIGS. 4a, 4b. The about centrally disposed microelectrode 134 is surrounded by four microelectrodes 134', 134", 134"', 134"", all of which are fully embedded in the support material 131. A distal terminal portion of the central microelectrode 134 is surrounded by a gel forming layer 137, which extends to the peripherally disposed microelectrodes 134, 134", 134"', 134"" and into the spaces between pairs of them. Similar to the microelectrode proto-set 120 of FIGS. 4a, 4b insertion of the proto-set 130 of microelectrodes immobilized in the layer of rigid support material dissolvable in body fluid into neural tissue results in the dissolution of the support material 131 followed by uptake of water by the gel forming layer 137, which results in its radial expansion combined with radial displacement of the terminal distal portions of the peripheral microelectrodes 134', 134", 134"', 134"" so as to make them fan out radially.

Figure 5:
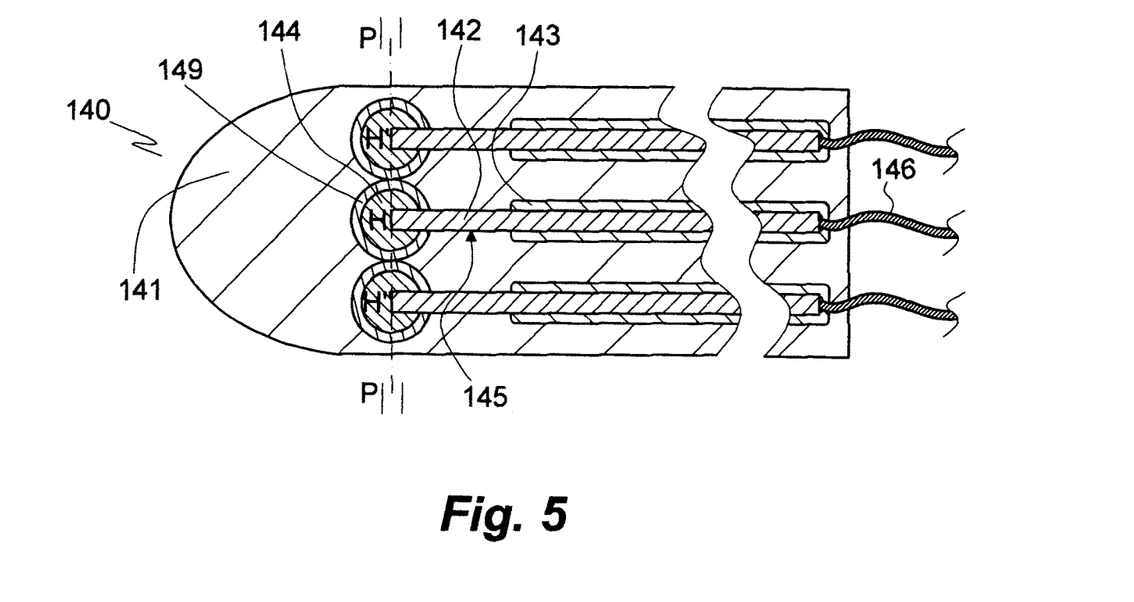
FIG. 5 illustrates a further embodiment of the set of proto-microelectrodes of the invention enclosed by a rigid support material dissolvable in body fluid, in an axial section (Q-Q, FIG. 5a)
Figures 5A, 5B:
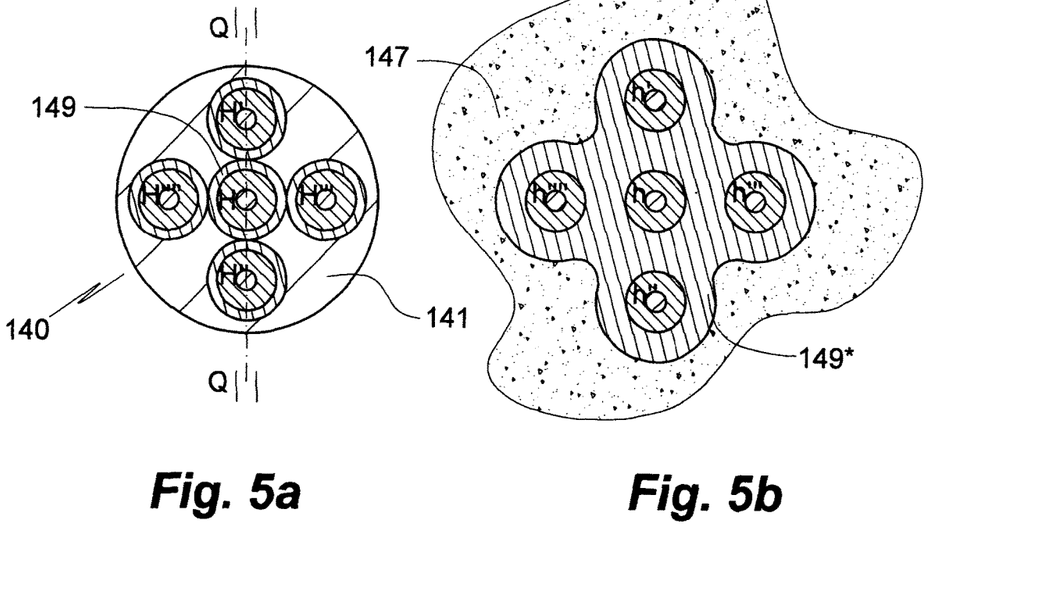
FIG. 5a illustrates the embodiment of FIG. 5 in a radial section (P-P, FIG. 5)
FIG. 5b illustrates a still further embodiment of the set of proto-microelectrodes of the invention in a radial section corresponding to that of FIG. 5a upon dissolution of the rigid support material and expansion of a gel forming material covering distal terminal bulge portions of the electrodes, resulting in forcing them radially apart.

The fourth embodiment 140 of the proto-set 140 of microelectrodes of the invention shown in FIGS. 5 and 5a comprises five microelectrodes H, H', H", H"', H"" of identical design embedded in a parallel aligned disposition in a rotationally symmetric layer of rigid support material 141 that is dissolvable in body fluid. At its proximal end each of the microelectrodes H, H', H", H"', H"" is provided with a flexible insulated wire 146 for establishing electrical communication with an implanted apparatus for electrode control (not shown). Only wire 146 is exemplarily identified in FIG. 5. The microelectrodes H, H', H", H"', H"" are of same design as the microelectrode of FIG. 1a except for their distal terminal bulge 144 (only identified for the central microelectrode H) being covered by a layer 149 (only identified for the central microelectrode H) of a material capable of forming a gel on contact with body fluid.

Upon insertion of the proto-set 140 of microelectrodes embedded in the layer 141 of rigid support material dissolvable in body fluid into neural tissue 147 the support material 141 is dissolved and the gel forming layers 149 on the terminal bulges 144 of microelectrodes H, H', H", H"', H"" are contacted by body fluid, which makes them expand and merge, as shown in FIG. 5b. The expansion of the gel 149* results in the distal terminal portions of the thus transformed peripherally disposed microelectrodes h', h", h"', h"" to be deflected radially outwardly from the central microelectrode h (identifies microelectrode H minus gel forming layer 149), so that their further insertion into neural tissue (not shown) results in making them fan out radially. Reference numbers 142, 143, 145 identify exemplarily for all electrodes H through H"" an electrode body, an insulating layer on the electrode body, and an annular non-insulated portion of the electrode body in contact with neural tissue.

Figure 6:
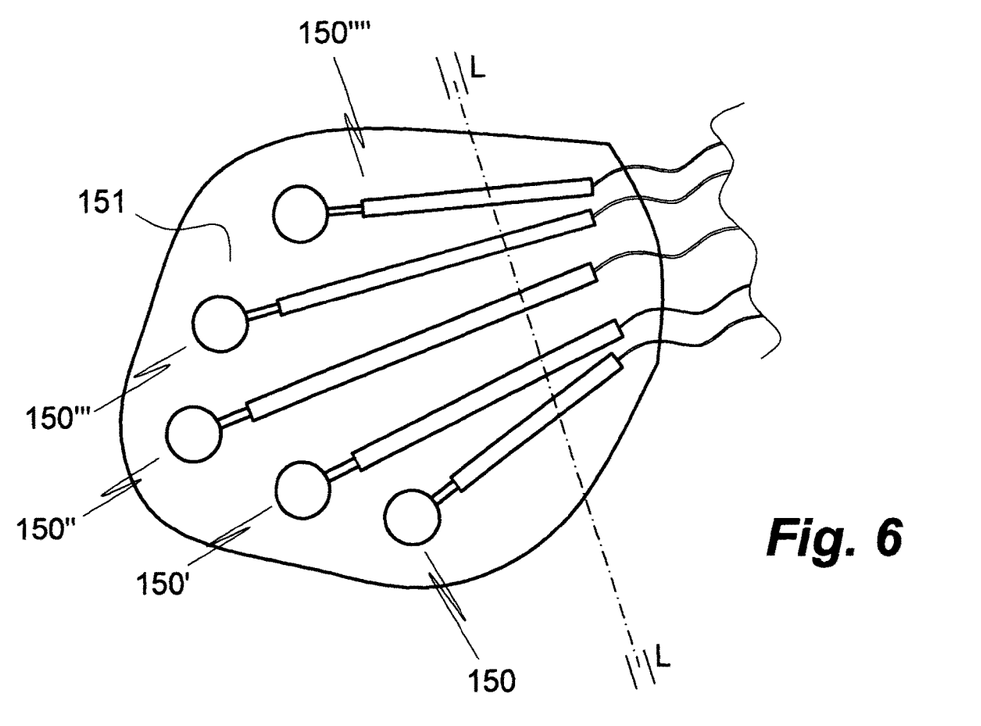
FIG. 6 illustrates a set of five proto-microelectrodes of the invention attached at their underside to one face of a gelatin sheet, in a top view.
Figure 6A:
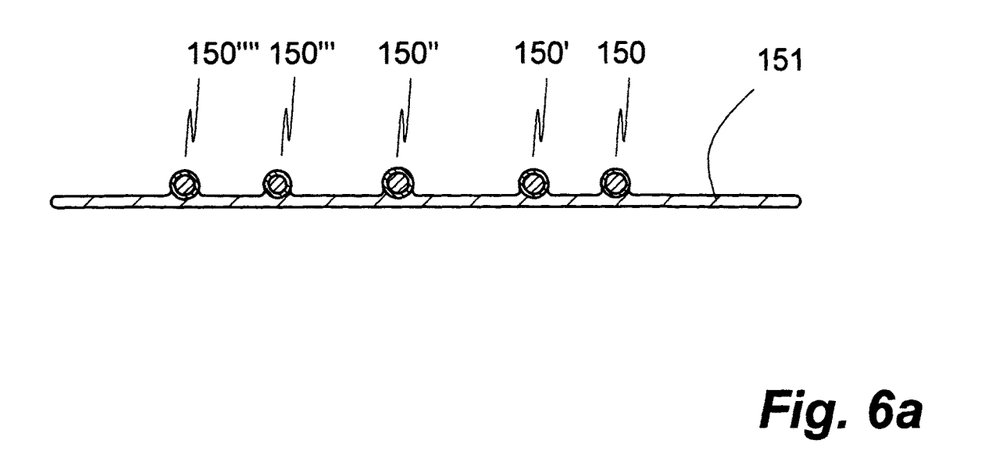
FIG. 6a is a transverse section L-L through the set of proto-microelectrodes of FIG. 6.

The proto-set of five microelectrodes 150, 150', 150", 150''', 150'''' of the invention shown in FIG. 6 is immobilized on the upper face a gelatin sheet 151 in a disposition with the front ends of the microelectrodes fanning out in a distal direction. Their immobilization is accomplished by moistening the area selected for disposing the microelectrodes on the gelatin sheet 151 to form a gel-like surface, disposing the microelectrodes 150, 150', 150", 150''', 150'''' on the gel-like surface in the desired disposition and pushing them against the surface, then drying to produce a permanent adhesive connection indicated exemplarily in FIG. 6a for microelectrode 150" by reference number 152. The microelectrodes 150, 150', 150", 150''', 150'''' are of same kind as the microelectrode of FIG. 1a. The thus immobilised set can be disposed, for instance, on either side of the dura mater where it is contacted by body fluid. Upon transformation of the dry gelatin sheet 151 into a gel and the dissolution of the gel the set of electrodes 150, 150', 150", 150''', 150'''' is disposed in or on the tissue in the desired configuration with each electrode being free to move or be displaced independent of the other electrodes. Since the dry gelatin sheet 151 is not flexible, it need to be made humid to allow bending it so as to make it abut a curved tissue surface. Alternatively the set of electrodes 150, 150', 150", 150''', 150'''' can be disposed on a sheet of dry gelatin already bent in a manner to make it fit with a particular tissue surface.

Figure 9:
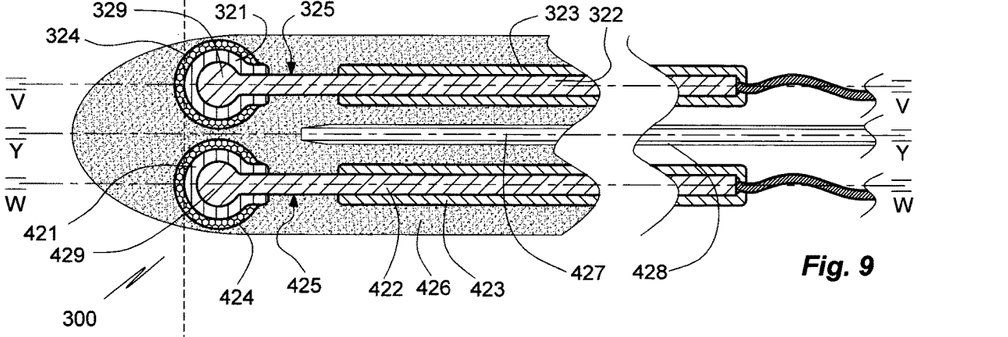
FIG. 9 is an axial section of a proto-set of two microelectrodes.

Example 3. Implantation of a Preferred Embodiment of a Proto-Set of Microelectrodes FIG. 9 shows a rotationally symmetric (axis Y-Y) proto-set 300 of two microelectrodes of FIG. 8, comprising oblong, rotationally symmetric (axes V-V, W-W) gold electrode bodies 322, 422 insulated by layers 323, 423 of Parylene C, distal gold bulbs 329, 429 integral with the bodies 322, 422, polyurethane caps 321, 421 covering the bulbs 329, 429, and sections 325, 425 free of insulation disposed between the insulated proximal and distal sections. The microelectrodes of the set and a centrally disposed cannula 428 comprising a through passage 427 are enclosed by and held by a glue matrix 426 that is easily dissolved by aqueous body fluid, for instance gelatin or glucose. To prevent premature dissolution and improve gliding properties the matrix 426 can be provided with a thin wax coat melting slightly above body temperature (not shown). Electrode axes V-V, W-W are disposed in parallel with the prot-set axis Y-Y.

Figure 9A:
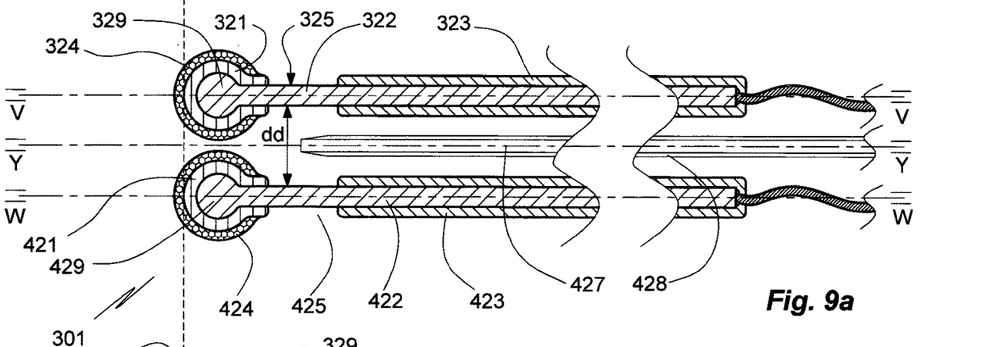
FIG. 9a shows the set of microelectrodes formed upon insertion of the proto-set into soft tissue and dissolution of the glue connecting the microelectrodes, in the same section.
Figure 9B:
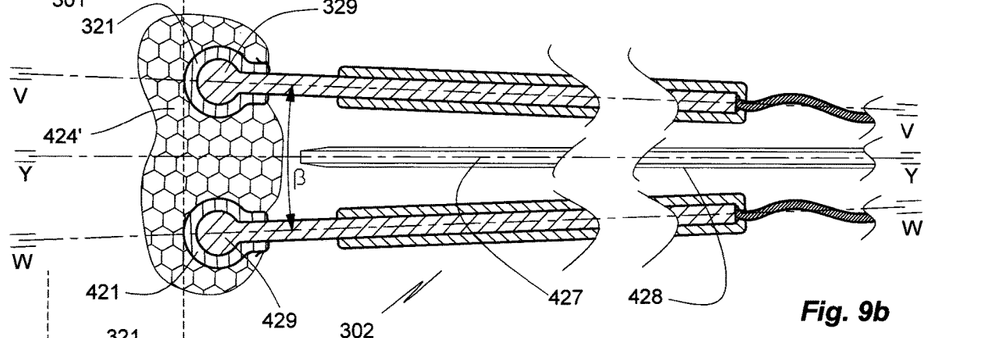
FIG. 9b shows the set of microelectrodes upon swelling of a layer of a material expandable in contact with aqueous body fluid disposed on their heads forcing their distal portions apart, in the same section.

Within a short time upon insertion, such as within a minute or a couple of minutes, the glue matrix 326 is dissolved. It can be removed by sucking it up through the cannula passage 427. FIG. 9a shows the set 301 of electrodes formed upon dissolution of the matrix 326 and removal of the aqueous solution formed. Reference numbers refer to same elements as in FIG. 9.

Figure 9C:
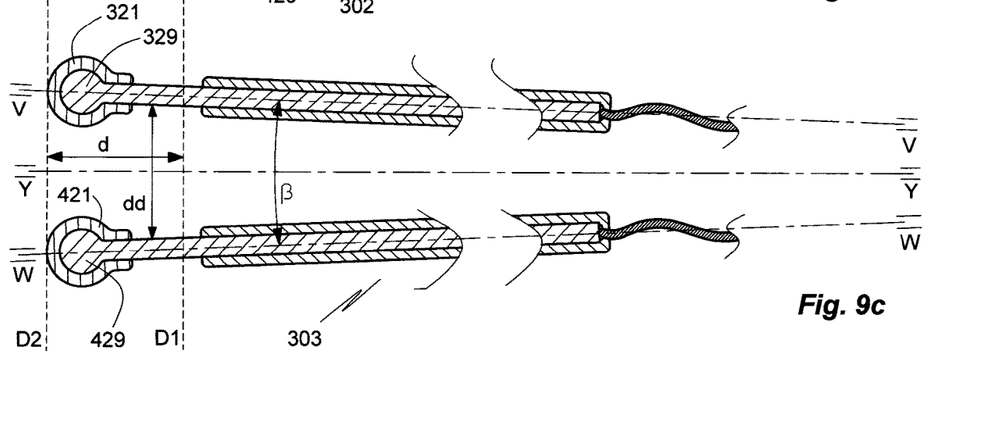
FIG. 9c shows the set of microelectrodes of FIG. 9b upon dissolution/degradation of the expandable material further inserted into the tissue, in the same section.

Holding the set 301 in the disposition of FIG. 9a for an extended period of time, such a for 30 min or more, allows the layer of expandable material 324, 424 on the caps 321, 421 to take up water from aqueous body fluid and to thereby expand so as to form a gel 424'. Expansion of portions of the layer 324, 424 disposed between the caps 321, 421 pushes the caps 321, 421 radially away from the central axis Y-Y, thereby changing the parallel disposition of the electrode bodies 322, 422 to an angular one (angle β) opening up in a distal direction. After dissolution/degradation of the gel 424 or after substantial softening of the gel 424 the electrodes 321, 322, 323, 329; 421, 422, 423, 429 can be further inserted (from depth D1 to depth D2, distance d) into the tissue along their axes V-V, W-W, so as to increase the distance dd between their insulation-free sections 325, 425 (FIG. 9c).

Materials

The electrode body is preferably of a noble metal or an alloy of noble metals or comprising noble metals such as gold, silver, platinum, iridium, but other biologically acceptable metals such as stainless steel and tantalum can also be used as well as gold plated copper. The metallic surface of the electrode body can be modified by applying a layer of another metal or metal alloy or a layer comprising or consisting of an electrically conducting non-metallic material such as titanium nitride, iridum oxide, platinum grey.

Alternatively the electrode body may consist of or comprise an electrically conducting polymer. Alternatively the electrode body can be made of a core of nonconductive polymer material coated with a metal, in particular a noble metal. The annular portions of the electrode body lacking insulation may be advantageously provided with surface enlarging elements or structures such as a roughened surface, forests of conducting nanowires, for instance carbon nanowires, or be porous. Surface enlarging structures of this kind will reduce the impedance of the electrode body. The electrode body can be connected with a control unit by an insulated separate electrical conductor coupled between the rear end of the electrode and the control unit or by the electrode body itself, a rear section thereof functioning as a coupling conductor. In such case the rear section is electrically insulated.

As a material for insulation of the electrode body suitable biocompatible polymer materials of all kinds can be used. The layer of insulating material can be applied by deposition of a monomer from the gas or liquid phase followed by polymerization on the electrode body or, such as for providing a silicone or Parylene C coat, dipping of the electrode body into a polymer or prepolymer solution, withdrawing it from the solution, and evaporating the solvent, optionally allowing a prepolymer to settle, is also useful. Suitable polymers comprise biocompatible types of polyurethane, polyurethane urea, polyimide, and Teflon®. An electrically insulating material of this kind can also be used for forming the bulge of the invention by locally applying a larger amount of it on the electrode body. Alternatively a polymer material different from that used for electrical insulation of the electrode body may be used such as, for instance, polyester or polyimide. The material of the bulge can comprise a visibility enhancing agent to improve its visibility in imaging techniques such as MRI or ultrasound.

The biocompatible electrode support material of the invention, which is soluble in body fluid, consists of or comprises water soluble carbohydrate or protein as well as their mixtures. A suitable rigid biocompatible material of this kind of which the dissolution rate can be controlled is obtained by repeatedly boiling and cooling an aqueous solution of a sugar or a mixture of sugars selected from sucrose, lactose, mannose, maltose and an organic acid selected from citric acid, malic acid, phosphoric acid, tartaric acid. By selecting particular combinations of sugar(s) and organic acid(s) it is possible to obtain materials with different dissolution times. Gelatin and various kinds of natural gums that are soluble in body fluid may also be used as a rigid biocompatible material. The biocompatible electrode support material of the invention can be applied on an electrode or on a set of electrodes by dipping it/them into an aqueous solution of the material followed by drying, which procedure can be repeated until a layer or shell of desired thickness has been formed on the electrode or set of electrodes. Alternatively spray coating can be used to apply layers of support material. Several layers can be applied in sequence, a drying step following upon each application.

Further useful electrode support materials include: arabinogalactan; arabinoxylan; galactan; galactomannan; lichenan; xylan; cellulose derivatives such as hydroxymethylpropyl cellulose and carboxymethyl cellulose; chitosan; gum Arabic; pullulan; polyvinylpyrrolidone; karaya gum; pectin; xanthane gum; tragacanth; alginic acid; heparan sulfate; RGD peptide; polyethylene oxide; chrondroitin sulfate; keratan sulfate; VEGF biomimetic peptide; perlecan (heparan sulfate proteoglycan 2); modified heparin; fibrin fragment; with the proviso that they are of sufficiently low molecular weight to make them soluble in body fluid.

The expandable material capable of swelling in body fluid for disposition between two or more microelectrodes in the vicinity of their distal ends in a proto-set microelectrodes of the invention is a material of a lower dissolution rate than the electrode support material. It is, for instance cross-linked gelatin or cross-linked hyaluronic acie. Other materials capable of forming protein gels can also be used, such as whey protein, soy protein, casein, but also one of the following agents: arabinogalactan; arabinoxylan; galactan; galactomannan; lichenan; xylan; cellulose derivatives such as hydroxymethylpropyl cellulose; chitosan; gum Arabic; carboxyvinyl polymer; sodium polyacrylate; carboxymethyl cellulose; sodium carboxymethyl cellulose; pullulan; polyvinylpyrrolidone; karaya gum; pectin; xanthane gum; tragacanth; alginic acid; polyoxymethylene; polyimide; polyether; chitin; poly-glycolic acid; poly-lactic acid; co-polymer of poly-glycolic and poly-lactic acid; co-polymer of poly-lactic acid and polyethylene oxide; polyamide; polyanhydride; polycaprolactone; maleic anhydride copolymer; poly-hydroxybutyrate co-polymer; poly(1,3-bis(p-carbophenoxy)propane anhydride); polymer formed by co-polymerization with sebacic acid or with poly-terephthalic acid; poly(glycolide-co-trimethylene carbonate); polyethylene glycol; polydioxanone; polypropylene fumarate; poly(ethyl glutamate-co-glutamic acid); poly(tert-butyloxy carbonylmethyl glutamate); poly-caprolactone; poly(caprolactone-co-butylacrylate); poly-hydroxybutyrate and copolymers thereof; poly(phosphazene); poly(D,L-lactide-co-caprolactone); poly(glycolide-co-caprolactone); poly(phosphate ester); poly(amino acid); poly(hydroxybutyrate); polydepsidpeptide; maleic anhydride copolymer; polyphosphazene; polyiminocarbonate; poly[(7.5% dimethyl-trimethylene carbonate)-co-(2.5% trimethlyene carbonate)]; polyethylene oxide; hydroxypropylmethylcellulose, poly(ethylene-co-vinyl acetate); isobutylene-based copolymer of isobutylene and at least one other repeating unit such as butyl acrylate: butyl methacrylate; substituted styrene such as amino styrene, hydroxy styrene, carboxy styrene, sulfonated styrene; homopolymer of polyvinyl alcohol; co-polymer of polyvinyl alcohol and at least one other repeating unit such as a vinyl cyclohexyl ether; hydroxymethyl methacrylate; hydroxyl- or amino-terminated polyethylene glycol; acrylate-based copolymer such as methacrylic acid, methacrylamide, hydroxymethyl methacrylate; ethylene vinyl alcohol copolymer; silicone based copolymer of aryl or alkyl siloxane and at least one repeating unit; polyurethane; heparan sulfate; RGD peptide; polyethylene oxide; chrondroitin sulfate; YIGSR peptides; keratan sulfate; VEGF biomimetic peptide; perlecan (heparan sulfate proteoglycan 2); Ile-Lys-Val-Ala-Val (IKVAV) containing laminin alpha-1 chain peptide; modified heparin; fragment of fibrin.

The friction reducing coat of the invention can comprise or consist of, for instance, Kollicoat® or shellack. It can be applied to the layer or shell of rigid biocompatible material by dipping the shell into an aqueous solution of the friction reducing agent followed by drying.

Implantation

The microelectrode or the set of microelectrodes of the invention can be implanted into soft tissue by insertion in their stabilized form by embedment in a layer or shell of rigid biocompatible material soluble in body fluid. Alternatively the microelectrode or set of microelectrodes can be implanted by disposing them in a cannula, inserting the cannula into soft tissue, and displacing the microelectrode or set of microelectrodes in a distal direction so as to make it or them protrude from the distal end of the cannula into the tissue, followed by withdrawal of the cannula.

An alternative method of implantation is by means of a cannula. The microelectrode or set of microelectrodes are disposed or disposed in an about parallel configuration in the cannula with its or their distal ends foremost; the cannula is inserted into the tissue to a desired depth; the microelectrode or set of microelectrodes is/are displaced in a distal direction by a force applied to their terminal proximal portion(s) so as to emerge from the distal opening of the cannula and be inserted into the tissue do a desired depth; the cannula is withdrawn, leaving the microelectrode(s) implanted in the tissue. The microelectrode or the set of microelectrodes can be also implanted in this manner in form of a proto-microelectrode or a proto-set of microelectrodes.

The invention claimed is:

1. A microelectrode for implantation into soft tissue comprising: an oblong, flexible electrode body of electrically conducting material having a proximal end and a distal end, the flexible electrode body comprising an insulated distal section and an insulated proximal section; wherein the insulated distal and insulated proximal sections are separated by an annular contact section that is not insulated and extends from the insulated distal section to the insulated proximal section, wherein the insulated proximal section includes the proximal end and is covered by a layer of a first insulating material that extends to the proximal end, wherein the distal section of the flexible electrode body comprises the distal end and a blunt distal terminal insulator bulge at the distal end;
   wherein the blunt distal terminal insulator bulge has a radial extension substantially greater than that of the insulated proximal section covered by the layer of the first insulating material, wherein the flexible electrode body is covered by the layer of the first insulating material and the blunt distal terminal insulator except for at the annular contact section disposed between the insulated distal section extending from the distal end in proximal direction to the annular contact section, and the insulated proximal section extending from the annular contact section to the proximal end, and wherein the microelectrode can only be implanted in soft tissue with a rigid support.

2. The microelectrode of claim 1, wherein the electrode body is rotationally symmetric and/or flexible or wherein the electrode body is flexible and curved and of a shape so as to be of rotationally symmetric form in a straight conformation.

3. The microelectrode of claim 2, wherein a distal face of the distal bulge is about hemispherical or hemi-elliptic or of paraboloid or hyperboloid form, and wherein the distal bulge comprises a circular or elliptic base facing in a proximal direction centred on the axis of rotational symmetry.

4. The microelectrode of claim 1, wherein said radial extension is greater by 50% or more than the radial extension of the layer of first insulating material on the proximal section.

5. The microelectrode of claim 1, wherein the axial length ratio of the distal section to the proximal section is 1:5 or more.

6. The microelectrode of claim 1, wherein the axial length of the annular section is 10% or less of the length of the electrode body.

7. The microelectrode of claim 1, wherein a layer of insulating material on the distal section is of a material different from that on the proximal section.

8. The microelectrode of claim 7, wherein a material capable of swelling in contact with aqueous body fluid is disposed on a layer of first and/or second insulating material covering the bulge, wherein the material capable of swelling has a Bloom strength of from 200 to 300 or more.

9. The microelectrode of claim 8, wherein swelling at body temperature and upon reaching equilibrium is by a factor of 2 or more.

10. The microelectrode of claim 7, wherein an insulating material disposed on the distal section is resilient.

11. The microelectrode of claim 10, wherein the resilient material comprises closed gas-filled cells.

12. The microelectrode of claim 1, attached or attachable to a flexible insulated electrical conductor, wherein the attachment is to the electrode body at or near the proximal end thereof in an electrically conducting manner.

13. The microelectrode of claim 1, wherein the electrode body is of a metal or comprises a metal.

14. The microelectrode of claim 1, wherein the electrode body is of an electrically conducting polymer or comprises such polymer.

15. A proto-microelectrode comprising or consisting of the microelectrode of claim 1 and a biocompatible solid support material, wherein the support material is attached to the microelectrode in a manner to stabilize it sufficiently so as to allow implantation thereof into soft tissue by insertion of the microelectrode with its distal end foremost, wherein the support material is rigid and is dissolvable in body fluid.

16. The proto-microelectrode of claim 15, wherein the support material consists of or comprises carbohydrate and/or protein and optionally comprises a pharmacologically active agent selected from the group consisting of coagulant, anticoagulant, antibiotic, osmotic pressure adjusting agent, anti-inflammatory agent, nutrient, factor stimulating growth, factor stimulating cell differentiation, hormone.

17. The proto-microelectrode of claim 15, wherein the support material encloses the microelectrode partially or fully.

18. A set of axially aligned proto-microelectrodes of claim 15 sharing said support material.

19. The set of claim 18, wherein the proto-microelectrodes are disposed in parallel or in a mode fanning out in a distal direction.

20. The set of claim 19, wherein two or more subsections of substantially greater diameter than that of the insulating layer on the proximal section differ in their radial extension.

21. The set of claim 18, wherein a microelectrode comprises one or more additional subsections of second insulating material of a radial extension substantially greater than that of the insulating layer on the proximal section, wherein said subsections are comprised by the distal and/or the proximal section.

22. The set of claim 21, wherein said subsections are separated by intermediate sections of smaller radial extension.

23. The set of claim 18, comprising an expandable material capable of swelling in body fluid disposed between two or more microelectrodes in the proximity of their distal ends, wherein the dissolution rate of material capable of swelling is lower than the dissolution rate of the support material and wherein said material capable of swelling has a Bloom strength of from 80 to 200.

24. The set of claim 18, wherein a distal bulge of insulating material is of non-spherical form.

25. The set of claim 24, wherein the distal bulge of non-spherical form is oblong and is axially disposed in such a manner so as to slant radially outwardly in respect of an axis of rotational symmetry of the layer.

26. The set of claim 18, wherein said two or more microelectrodes differ in the composition of insulating material forming their distal bulges and/or forming one or more of said subsections so as to allow identification of individual microelectrodes implanted in nervous tissue by radiative means.

27. The set of claim 18, comprising microelectrodes of different length.

28. The proto-microelectrode of claim 15, further comprising a friction reducing coat on the support material.

29. A method of implanting a microelectrode in soft tissue, comprising:
   providing a proto-microelectrode according to claim 15;
   inserting the microelectrode with its distal end foremost; and
   allowing body fluid to dissolve the support material.

30. The method of claim 29, comprising disposing the proto-microelectrode in a cannula with its distal end foremost; inserting the cannula into the tissue, displacing the proto-microelectrode within the cannula to make it emerge through the front opening thereof and to further displace it in a distal direction to a desired depth; withdrawing the cannula; allowing body fluid to dissolve the support material.

31. The microelectrode of claim 1, wherein the blunt distal terminal insulator bulge is formed by one of:
   a layer of first insulating material on the distal section;
   a layer of first insulating material on the distal section covered or fully or partly substituted by a layer of a second insulating material; and
   a layer of first insulating material and/or second insulating material on the bulb.

* * * * *